United States Patent [19]

Beldzisky

[11] Patent Number: 4,479,272
[45] Date of Patent: Oct. 30, 1984

[54] PROSTHESIS RETAINER

[76] Inventor: David Beldzisky, 191 Rue Saint Charles, 75015 Paris, France

[21] Appl. No.: 462,371

[22] Filed: Jan. 31, 1983

[30] Foreign Application Priority Data

Feb. 5, 1982 [FR] France ................. 82 01855

[51] Int. Cl.³ .................... A61F 1/08; A61F 1/02; A61F 1/14
[52] U.S. Cl. ............................................. 3/16; 3/19
[58] Field of Search ............................. 3/16–19, 3/22, 2

[56] References Cited

U.S. PATENT DOCUMENTS

| 3,262,131 | 7/1966 | Argersinger | 3/17 R |
| 3,600,717 | 8/1971 | McKeehan | 3/19 |

FOREIGN PATENT DOCUMENTS

| 675386 | 5/1966 | Belgium | 3/19 |
| 851394 | 10/1952 | Fed. Rep. of Germany | 3/22 |
| 1135516 | 12/1956 | France | 3/17 R |
| 71219 | 4/1959 | France | 3/17 SS |
| 73157 | 4/1960 | France | 3/19 |
| 1532625 | 6/1968 | France | 3/18 |
| 826041 | 12/1959 | United Kingdom | 3/19 |
| 1076560 | 10/1967 | United Kingdom | 3/19 |

Primary Examiner—Ronald L. Frinks
Attorney, Agent, or Firm—Weiser & Stapler

[57] ABSTRACT

A plurality of sheaths extend along the sleeve of a socket prosthesis. The outermost, or retaining sheath is open at top and bottom and extends from above the sleeve down over the prosthesis itself. Different portions of the retaining sheath have different degrees of elasticity. An inner sheath is first folded over the top edge of the retaining sheath, and then folded again, together with the retaining sheath, to form a welt which abuts against the upper edge of the prosthesis sleeve.

6 Claims, 4 Drawing Figures

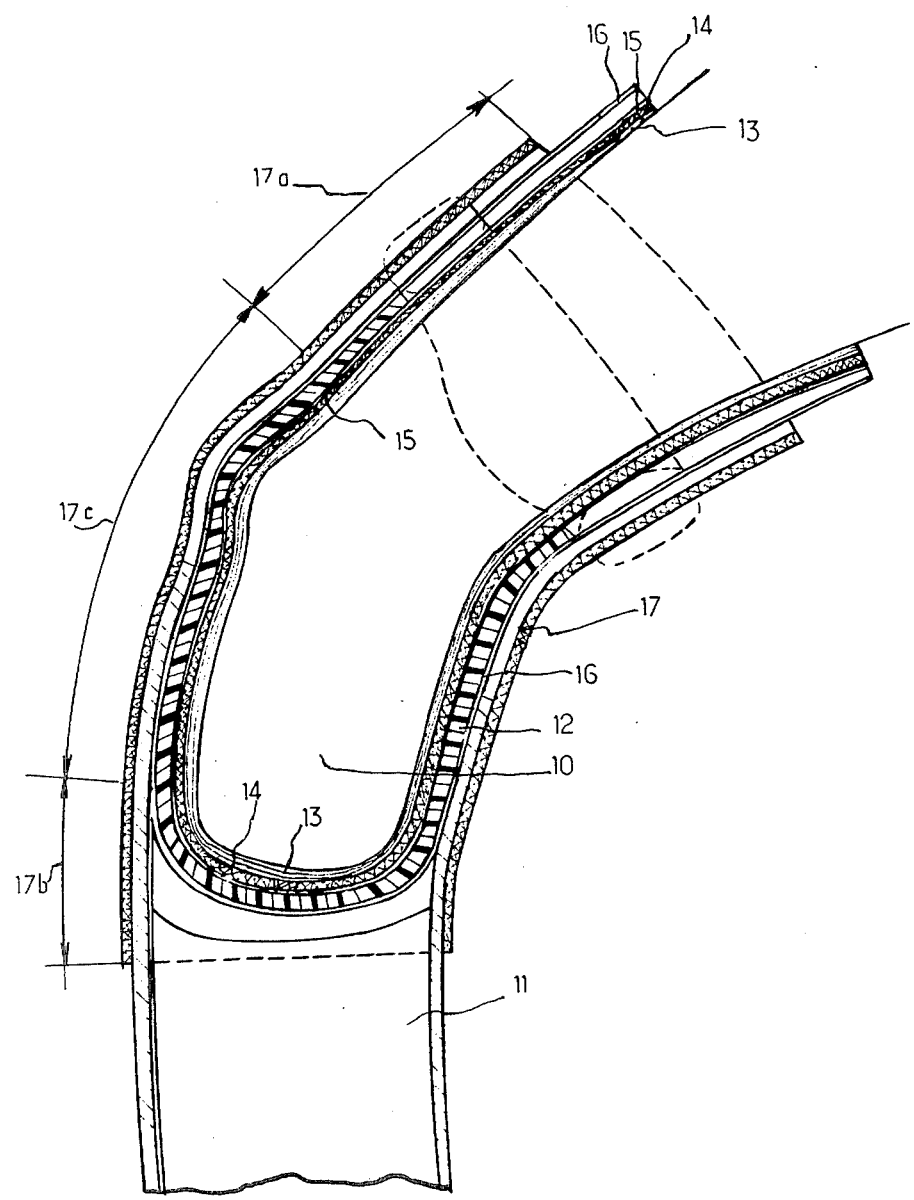
FIG: 1

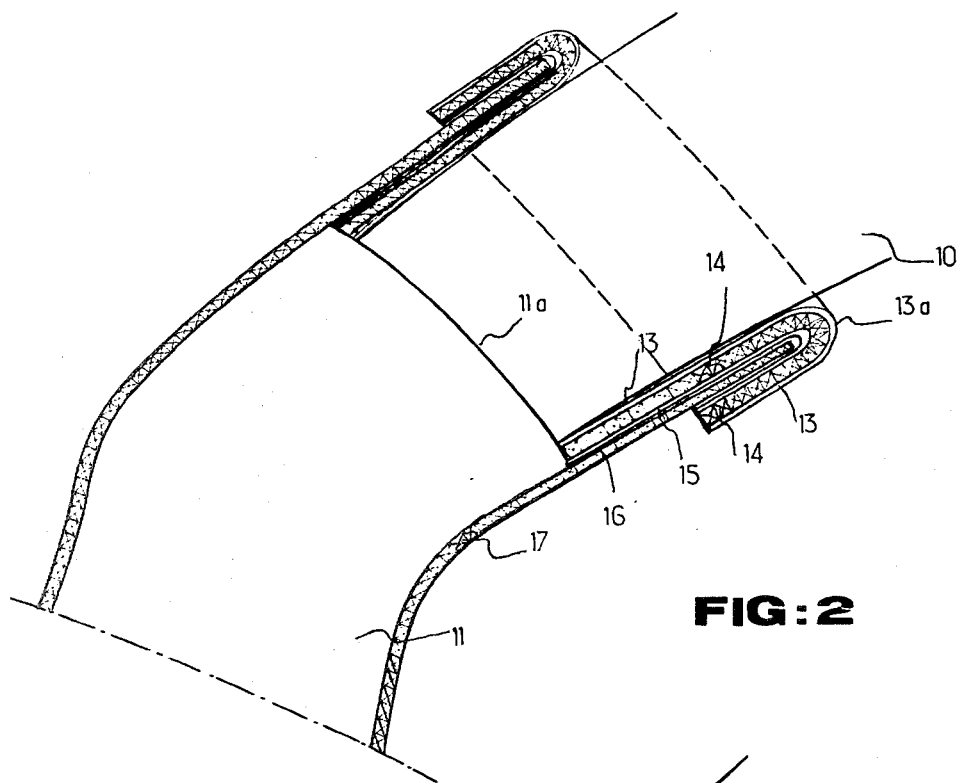
FIG:2
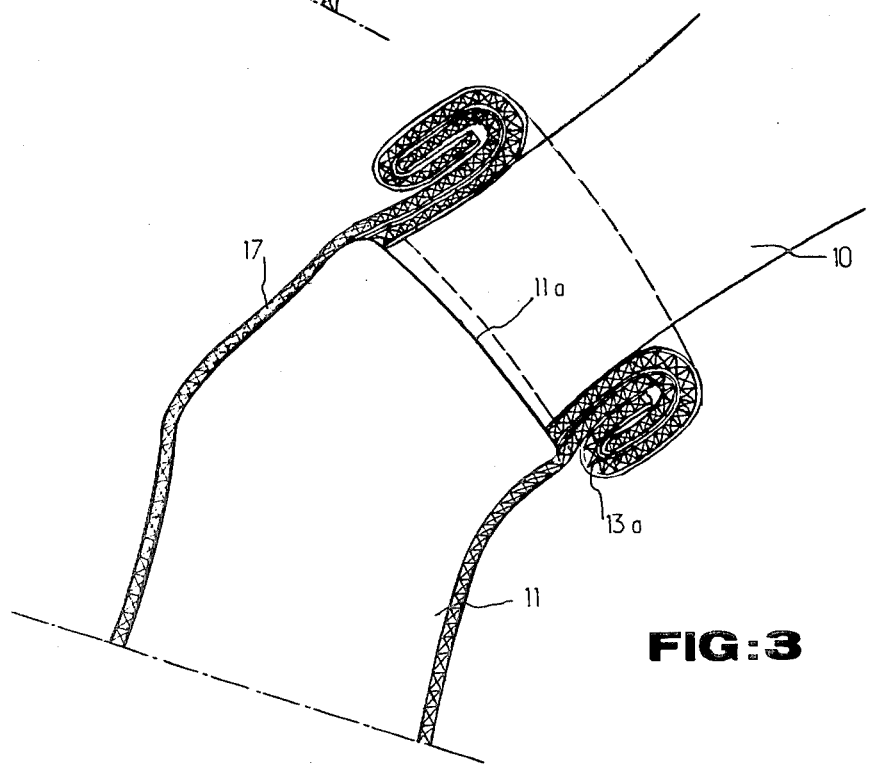
FIG:3

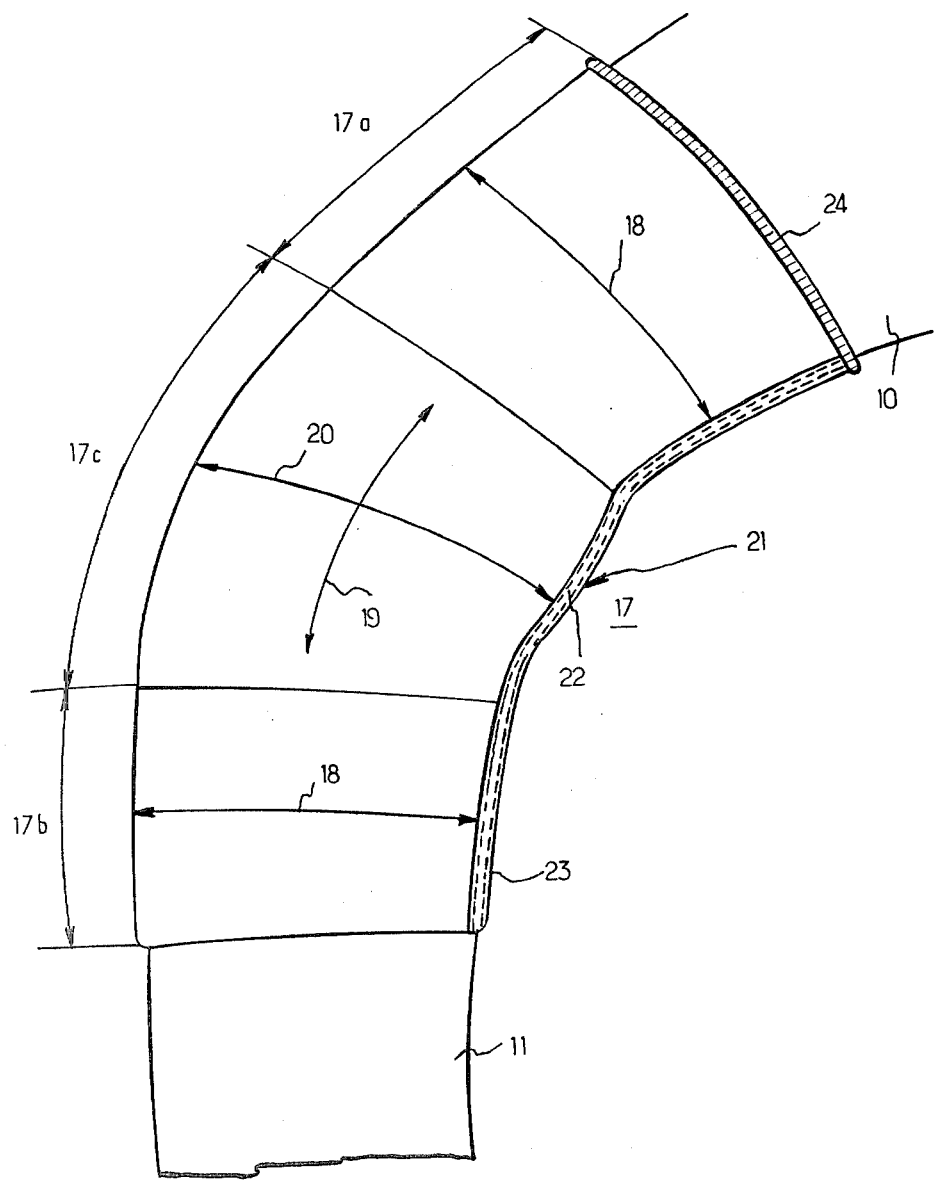
FIG: 4

PROSTHESIS RETAINER

The invention relates to apparatus which is particularly suitable for the protection of amputated limbs and for the application of prostheses.

From French Patent No. 1,135,516 of Sept. 16, 1955, there is already known a protective arrangement for amputees who use prosthetic devices. This arrangement comprises a fine stocking with low friction coefficient, this contact stocking being applied to the amputated member, as a result of which there are reduced inflammations, abrasions, and all other problems resulting from the friction which is caused by the wearing of a prosthetic device, particularly in case of amputation of a lower member.

From Certificate of Addition 71,219 to the above-mentioned patent, there is also known the use of a combination consisting of a nylon contact sheath and a stump covering bonnet, e.g, of wool, pulled over the sheath in such a way that the amputated member is always protected by the fine sheath which can slide within the wool bonnet while the latter provides, externally, a frictional coefficient higher than that of the sheath. This makes it possible to stabilize it relative to the walls of a prosthesis sleeve or of a prosthesis, whereby the protection is increased and the comfort enhanced. To prevent the use of the contact sheath from forming injurious folds, affixation of the contact sheath and of the stump covering bonnet is provided by folding both sheath and bonnet over the upper edge of the prosthesis. This method of protection prevents sliding of the contact sheath with respect to the amputated member and also formation of harmful folds.

Although this arrangement constitutes a substantial progress in the wearing of prostheses, particularly those for leg amputations without socket, their use nevertheless exhibits with the method of affixation that has just been described, an effect of slight pumping of the contact sheath and of the bonnet within the sleeve of the prosthesis due to the fact that the member is more or less well matched to the prosthesis despite the affixation folds over the prosthesis. Thus, during walking, while climbing stairs, while entering a car, each lifting movement of the lower amputated member produces a relative disengagement movement which, after a while, causes discomfort, tires the amputated member which is always sensitive to alternative pumping movements relative to the prosthesis, and can also cause irritation and abrasions.

Accordingly, the principal objective of the present invention is to provide an arrangement which assures both skin protection for an amputated limb, particularly a lower limb, and correct retention of the protected limb against a prosthesis.

Another object of the invention is to provide a protection and retention arrangement which practically suppresses, during wearing of a prosthesis, the pumping effect which is hard to tolerate.

Still another object of the invention is to provide an arrangement which very substantially improves the tolerance to the wearing of prostheses.

These objects and others which will appear are achieved in accordance with the invention by an arrangement which comprises in combination a first fine contact sheath for skin protection associated with a stump covering bonnet, e.g, of wool, a second fine sheath which covers the bonnet, has a low coefficient of friction and is in contact internally with a prosthesis sleeve, a third fine sheath which covers the sleeve and also has a low coefficient of friction and is in contact with the socket of the prosthesis, and finally a prosthesis retaining sheath of elastic material, open at both ends, covering a portion of the prosthesis and having in the vicinity of its respective open ends an upper elastic retention portion and a lower elastic retention portion, and an intermediate articulation portion, the upper end portion providing partial coverage of the corresponding upper portions of the fine contact sheaths, of the bonnet, of the fine bonnet covering sheath, and of the fine sleeve covering sheath. The respective lengths of the first sheath and of the bonnet, and of the second and third fine sheaths, are such that they are folded back once by simply turning them over upon the upper end portion of the prosthesis retaining sheath, and a second time together with said upper end portion of the prosthesis retaining sheath in such manner as to form a flat elastic retention welt, one of whose edges contacts the upper opening edge of the prosthesis socket.

Due to this overall arrangement, the retention welt buts against the upper edge of the prosthesis, thereby preventing pumping movements between the protected limb and the prosthesis.

The edge of the prosthesis retaining sheath which is trapped within the double fold of the retention welt provides permanent tension for sheaths and bonnet.

The second bonnet covering sheath enables, in the region of articulation, a relative angular displacement between the first fine stocking and its bonnet relative to the engagement sleeve.

The third sleeve covering sheath provides for sliding engagement of the sleeve within the prosthesis socket.

The overall arrangement axially immobilizes the amputated member relative to the prosthesis, but permits and facilitates angular movements in the region of articulation, the second and third sheaths performing the function of a sliding bearing.

In one embodiment, the two end portions of the prosthesis retaining elastic sheath are axially non-stretchable but radially stretchable in elastic manner.

In another embodiment, the prosthesis retaining sheath has its middle portion doubly stretchable relatively slightly in the axial direction, and more so in the radial direction in the region of articulation of the protected member.

Still other arrangements will appear from the detailed description of an embodiment which follows and which is provided here by way of example in the attached drawings, wherein:

FIG. 1 is a sectional view showing the different components of the arrangement in actual use, in conjunction with a leg prosthesis of the type having an engagement sleeve.

FIG. 2 is a partial sectional view, similar to FIG. 1 and showing the first stage of assembly of the components of the arrangement.

FIG. 3 is a partial sectional view, similar to FIG. 1, and showing the second stage of retention of the components relative to the prosthesis.

FIG. 4 is a view of the prosthesis retainer of the arrangement, mounted upon the prosthesis, but before retention.

In the illustrative embodiment of FIG. 1, there is shown the application of the arrangement to the wearing of a prosthesis upon an amputated lower limb designated by reference numeral 10. In this instance, the amputation is substantially below the knee.

The prosthesis 11 is of the type having an engageable sleeve 12 known in itself, which may for example be of molded elastomer.

The means for epidermal protection of the amputated limb comprises a first fine contact sheath 13, knitted like a stocking of fine synthetic thread specially treated to insure complete lack of reaction to contact with the skin. The first sheath is covered by a stump covering bonnet 14, for example a wool bonnet, providing a shock absorbing layer and also a perspiration absorbing layer whereby there is eliminated one of the causes of irritation of a protected amputated member. In case of a socket leg prosthesis, as shown in FIG. 1, it has been found particularly desirable to use a second fine sheath 15, i.e. a bonnet covering sheath, having a low coefficient of friction which covers the bonnet 14 and which provides a dual function; the sheath 15 permits easy engagement of the elastomeric retention sleeve 12 over the contact sheath and the stump covering bonnet. It will be understood that this arrangement causes the sheath 15 to behave like a bearing between the stump covering bonnet and the inner surface of the elastomeric sleeve 12, thereby making angular bending movements much easier during articulation in the region of the knee.

Sleeve 12 is covered by a third fine sheath 16 having a low coefficient of friction, similar to the two first ones, and having as its purpose to facilitate the introduction of sleeve 12 into the prosthesis socket 11, and also to facilitate the angular articulation movements between the sleeve and the prosthesis itself.

The arrangement further includes a prosthesis retaining sheath 17 of essentially elastic material, which grips the body of the prosthesis through elastic contraction. The prosthesis retaining sheath is open at both ends and includes an upper elastic retention portion 17a, a lower elastic retention portion 17b, and an intermediate articulation portion 17c. The structure of the prosthesis retaining sheath is more particularly described in relation to the example of FIG. 4.

It will be noted that the contact sheath 13, the bonnet 14, and the two sheaths 15 and 16 are substantially longer than the elastic prosthesis retaining sheath 17. This makes it possible, as shown in FIGS. 2 and 3, to assemble the components of the arrangement and to retain them relative to the upper edge 11a of the prosthesis.

In the example of FIG. 2, the first sheath 13, the stump cover bonnet 14, and the sheaths 15 and 16 are folded once over the upper retention portion of the prosthesis retaining sheath 17. There is then formed a second retaining fold, as shown in FIG. 3, which forms with the first fold a compression welt, one of whose edges 13a contacts edge 11a of the sleeve opening of prosthesis 11. It will be understood that, by this arrangement, the components of the device are assembled to each other, the sheaths and the stump covering bonnet are stretched and, with the welt butting up against the upper edge of the prosthesis, all axial displacement of the prosthesis relative to the protected member is precluded.

To provide the functions of assembly, attachment and relative movement, particularly of bending in the region of articulation, sheath 17 has a specific structure which is detailed in FIG. 4.

First of all, the prosthesis retaining elastic sheath has the peculiarity that its two end portions, namely 17a and 17b, are axially non-stretchable, but are radially elastically stretchable in the direction of arrows 18. The middle portion 17c of the prosthesis retaining sheath has double stretchability, relatively slight in the axial direction as indicated by arrow 19, the other more pronounced in the radial direction as indicated by arrow 20 in the region of articulation of the protected member. It will be understood that, due to this different elasticity in the axial and radial directions, the middle portion 17c of the sheath adapts to the natural deformations of articulation, particularly bending. To facilitate this bending, there is also provided in the middle region 17c, upon the posterior generatrix 21 in the region of bending of the articulation, a slight increase in diameter which is indicated in the drawing by a convex portion 22. This facilitates, during bending of the articulation, the formation of an external fold which does not impede the bending function.

The prosthesis retaining sheath has, all along its posterior generatrix 21, a substantially unstretchable band 23 formed, for example, by a strip of cloth which is non-stretchable and is sewed along this generatrix. Its function is to prevent the possibility of stretching this sheath during walking movements, particularly in the posterior-anterior direction. It will also be noted that the prosthesis retaining stocking has a marker welt 24 at the edge of its upper opening.

The complete arrangement provides a degree of well being never obtained in the wearing of prostheses, and particularly of those for lower limbs, because of the extremely low coefficient of friction in the region of articulation and because of the absence of the pumping effect.

It will be understood that the invention is not limited to the illustrative embodiments described and shown above, which may have other variants or adaptations without thereby departing from the scope of the appended claims.

I claim:

1. An arrangement for the epidermal or protection of an amputated limb, e.g., a lower limb, and for retention of the protected member relative to a prosthesis, the arrangement comprising in combination:

a first fine contact sheath for epidermal protection associated with a stump covering bonnet, e.g, of wool, a second bonnet covering fine sheath having a low coefficient of friction and in internal contact with a sleeve affixable to the prosthesis, a third fine sheath having a low coefficient of friction covering the bonnet and in contact with the socket of the prosthesis, a prosthesis retaining sheath of elastic material open at both ends, covering the prosthesis and having in the vicinity of its two open ends respectively an upper and lower elastic retention portion, and an intermediate middle portion partially covering the corresponding upper portions of the fine contact sheath, the bonnet, the bonnet covering fine sheath and the sleeve covering fine sheath, the respective lengths of the first sheath and bonnet, and of the second and third fine sheaths being such that they are folded over once by simple turning over the upper end of the prosthesis retaining sheath and then a second time together with same to form an elastic retaining welt, one of whose edges is in contact with the edge of the upper aperture of the prosthesis socket.

2. The arrangement of claim 1, wherein the prosthesis retaining elastic sheath has its two end portions non-stretchable axially, but elastically stretchable radially.

3. The arrangement of claim 1 wherein the elastic prosthesis retaining sheath has a middle portion which provides double stretchability, a relatively slight one in the axial direction and one which is more pronounced in the radial direction in the region of articulation of the protected limb.

4. The arrangement of claim 1 wherein the middle portion of the prosthesis retaining sheath has upon its posterior generatrix, in the region of bending of the articulation, an increased diameter which facilitates the bending function.

5. The arrangement of claim 1 wherein the prosthesis retaining sheath has, all along its posterior generatrix, a substantially non-stretchable band, whose function it is to limit the amplitude of extension during walking movements in the posterior-anterior direction.

6. The arrangement of claim 1 wherein the prosthesis retaining sheath has a marker welt at the edge of its upper aperture.

* * * * *